United States Patent [19]

Moncada

[11] 4,393,063

[45] Jul. 12, 1983

[54] TREATMENT FOR GASTRIC LESIONS

[75] Inventor: Salvador E. Moncada, West Wickham, England

[73] Assignee: Burroughs Wellcome Co., Research Triangle Park, N.C.

[21] Appl. No.: 280,853

[22] Filed: Jul. 6, 1981

Related U.S. Application Data

[62] Division of Ser. No. 907,355, May 18, 1978, Pat. No. 4,337,254.

[30] Foreign Application Priority Data

Aug. 23, 1977 [GB] United Kingdom ............... 35261/77

[51] Int. Cl.³ .................. A61K 31/34; A61K 31/44; A61K 31/52; A61K 31/505
[52] U.S. Cl. .................................. 424/251; 424/253; 424/258; 424/263; 424/285
[58] Field of Search ................. 424/25.3, 25.1, 28.5, 424/258, 263

[56] References Cited

U.S. PATENT DOCUMENTS

| | | | |
|---|---|---|---|
| 3,954,787 | 5/1976 | Monkhouse | 424/305 |
| 3,962,243 | 6/1976 | Roldan et al. | 424/253 |
| 3,998,953 | 12/1976 | Konz et al. | 424/253 |
| 4,009,282 | 2/1977 | Voorhees | 424/305 |
| 4,051,236 | 9/1977 | Harris et al. | 424/93 |
| 4,158,667 | 6/1979 | Axen | 424/269 |

FOREIGN PATENT DOCUMENTS 2431558 1/1975 Fed. Rep. of Germany.
2739277 3/1978 Fed. Rep. of Germany.

*Primary Examiner*—Douglas W. Robinson
*Attorney, Agent, or Firm*—Donald Brown

[57] ABSTRACT

Pharmaceutical combinations comprising (a) prostacyclin, dihydroprostacyclin or a pharmaceutically acceptable salt of either of these, and (b) a phosphodiesterase inhibitor. Pharmaceutical formulations comprising a combination as above and a pharmaceutically acceptable carrier. Methods are disclosed for preparing the combinations and the formulations.

The combinations and formulations are useful for preventing or minimising platelet aggregation in blood, blood products or blood substitutes for example in the treatment of thrombosis, gastric lesions and wounds, and in the extra-corporeal circulation of blood and in blood separation processes.

4 Claims, No Drawings

TREATMENT FOR GASTRIC LESIONS

This is a division of application Ser. No. 907,355 filed May 18, 1978, now U.S. Pat. No. 4,337,254.

The present invention relates to the use in medicine of prostacyclin or its dihydro derivative or their salts in conjunction with a phosphodiesterase inhibitor and to a pharmaceutical formulation containing them.

Prostacyclin (PGX or PGI$_2$) and its dihydro derivative (9-deoxy-6$\xi$,9$\alpha$-epoxy prostaglandin F$_{1\alpha}$) and their salts, including their sodium salts, (hereinafter referred to as the "active compounds") exhibit a potent anti-aggregatory action on blood platelets and therefore have particular utility as anti-thrombosis agents in the treatment and/or prophylaxis of mammals, including man. The active compounds may also be used in mammals, including man, to reduce and control excessive gastric secretion, thereby reducing or avoiding gastrointestinal ulcer formation, and accelerating the healing of ulcers already present in the gastrointestinal tract.

The active compounds also affect the biochemical cooperation between platelets and vascular endothelium which contributes to the repair of damaged vascular endothelium. Therefore, the active compounds have a further utility in the treatment of wound healing in mammals, including man.

The active compounds are useful whenever it is desired to inhibit platelet aggregation, or induce disaggregation of platelet aggregates (these related effects on platelet aggregation are regarded as in essence equivalent for the purposes of this specification and claims). The active compounds also reduce the adhesive character of platelets, and are used to treat or prevent the formation of thrombi in mammals, including man. For example, these compounds are useful to treat or prevent myocardial infarcts, to treat or prevent post-operative thrombosis, to promote patency of vascular grafts after surgery, and to treat complications of arteriosclerosis and conditions such as atherosclerosis, blood clotting defects due to lipemia, and other clinical conditions in which the underlying etiology is associated with lipid imbalance or hyperlipidemia.

The active compounds are especially useful as additives to blood, blood products, blood substitutes and other fluids which are used in artificial extra-corporeal circulation and perfusion of an isolated body portion, e.g. a limb or an organ, whether attached to the original body, detached and being preserved or prepared for transplant, or attached to a new body. During these circulations and perfusions, aggregated platelets tend to block blood vessels and portions of the circulation apparatus. This blocking may be avoided by the presence of the active compounds. For this purpose, the compound may be added gradually or in single or multiple portions to the circulating blood, to the blood of the donor animal, to the perfused body portion, detached or attached, to the recipient, or to two or all of these at a total steady state dose of from 0.001 to 10 mg. per liter of circulating fluid. It is useful to use these compounds in laboratory animals, e.g. cats, dogs, rabbits, monkeys and rats, for these purposes to developed new methods and techniques for organ or limb transplant.

In addition to the above described effects the active compounds also exhibit a vasodilatory action on blood vessels. There are often occasions when it would be desirable to be able to utilise the other effects described above (notably the anti-aggregatory effects) while at the same time suppressing or eliminating the vasodilatory effect of the active compounds, for example in the treatment or prevention of myocardial infarcts and when used as an addition in extra-corporeal circulation. It is with the mitigation or avoidance of this vasodilation complication that the present invention is concerned.

We have now surprisingly discovered that the anti-aggregatory effects, but not the vasodilatory effects of the active compounds are potentiated by chemical compounds exhibiting a particular pharmacological activity. This discovery provides a means to dissociate the anti-aggregatory effects from the vasodilatory effects of the active compounds.

Accordingly the present invention provides a pharmaceutical combination which comprises:
(a) prostacyclin, dihydroprostacyclin or a pharmaceutically acceptable salt of either of these and
(b) a phosphodiesterase inhibitor.

The combination promotes an anti-aggregatory action on blood platelets.

The use, in combination, of an active compound and a phosphodiesterase inhibitor lowers the anti-aggregatory threshold level (the minimum amount of active compound required to exhibit anti-aggregatory effects) without substantially affecting the vasodilatory threshold level.

Thus by administering an active compound at a concentration below its vasodilatory threshold level, but above the new, lower, anti-aggregatory threshold, together with a phosphodiesterase inhibitor, anti-aggregatory effects can be produced whilst vasodilatory effects are not.

It is known that the active compounds can stimulate the production, in blood platelets, of cyclic AMP and it has been suggested that the anti-aggregatory effects of the active compounds may be attributable to the formation of cyclic AMP. Phosphodiesterase inhibitors inhibit the breakdown of cyclic AMP and so it may be that the potentiation of the anti-aggregatory effects occurs because in the presence of a phosphodiesterase inhibitor an adequate, anti-aggregatory, concentration of cyclic AMP can be obtained with a smaller concentration of active compound.

The mechanism by which the active compounds manifest their vasodilatory effects is not known, although a link between cyclic AMP concentration and vasodilatory activity has been suggested for other compounds. Our discovery that the vasodilatory effects of the active compounds used in the present invention are not potentiated by phosphodiesterase inhibitors suggests that cyclic AMP is not involved in the vasodilatory effect of the active compounds.

Suitable phosphodiesterase inhibitors for use in potentiating the anti-aggregatory effects of the active compounds include:

Xanthine derivatives such as:
Theophylline {3,7-dihydro-1,3-dimethyl-1H-purine-2,6-dione}, and salts thereof.
3-Isobutyl-1-methyl-xanthine;
Caffeine {3,7-dihydro-1,3,7-trimethyl-1H-purine-2,6-dione} and salts thereof; and
Aminophylline {adduct of Theophylline and 1,2-ethanediamine (2:1)}.

Phosphodiesterase inhibitors other than xanthine derivatives that may be used in the combinations of the present invention include, as such or as pharmaceutically acceptable salts:

(a) Isoquinoline derivatives, for example:
Papaverine {1-[(3,4-dimethoxyphenyl)methyl]-6,7-dimethoxyisoquinoline} and salts thereof; and
6,7-Diethoxy-1-(4,5-diethoxybenzyl)isoquinoline or its salts e.g. its hydrochloride;
(b) Derivatives of pyrimido {5,4-d}pyrimidine, for example
Dipyridamole {2,2',2'',2'''-(4,8-dipiperidinopyrimido[5,4-d]pyrimidin-2,6-diyldinitrilo)tetraethanol} and its salts;
2,2',2'',2''',-[[4-(1-piperidinyl)pyrimido[5,4-d]pyrimidin-2,6-diyl]dinitrilo]tetrakisethanol and its salts; and
2,4,6-tri-4-morpholinylpyrimido[5,4-d]pyrimidine and its salts.
(c) Derivatives of thieno[3,2-d]pyrimidine, for example N-[4-(4-morpholinyl)thieno]3,2-d[pyrimidin-2-yl]-1,2-ethanediamine.
(d) Derivatives of pyrazolo[3',4':2,3]pyrido[4,5-b][1,5]benzodiazepin-6-(3H)-one, for example
3-Ethyl-7,12-dihydro-7,12-dimethyl-pyrazolo[4',3':5,6]pyrido[4,3-b]-[1,5]benzodiazepin-6-(3H)-one;
3-Ethyl-7,12-dihydro-9-methoxy-7,12-dimethyl-pyrazolo[3',4':2,3]pyrido[4,5-b][1 5]benzodiazepin-6-(3H)-one; and
10-Chloro-3-ethyl-7,12-dimethyl-7,12-dihydropyrazolo[4',3':5,6]pyrido[4,3-b][1,5]benzodiazepin-6-(3H)-one;
(e) Derivatives of 1H- or 2H-pyrazolo[3,4-b]pyridine, for example
4-(Butylamino)-1-ethyl-1H-pyrazolo[3,4-b]pyridine-5-carboxylic acid ethyl ester;
4-(Butylamino)-1H-pyrazolo[3,4-b]pyridine-6-carboxylic acid ethyl ester;
4-Chloro-1-ethyl-3-methyl-1H-pyrazolo[3,4-b]pyridine-5-acetonitrile;
1-Ethyl-4-(isopropylidenehydrazino)-3-methyl-1H-pyrazolo[3,4-b]pyridine-5-carboxylic acid ethyl ester or its salts such as its hydrochloride hemihydrate; and
2-Methyl-6-phenyl-4-(1-piperidinyl)-2H-pyrazolo[3,4-b]pyridine or its salts e.g. its hydrochloride.
(f) Derivatives of 5H-furo-[3,4-e]pyrazolo[3,4-b]pyridine-5-one, for example
4-(Butylamino)-1-ethyl-1,7-dihydro-7-hydroxy-5H-furo-[3,4-e]pyrazolo[3,4-b]pyridine-5-one; and
(g) Derivatives of 1(2H)-naphthalenone, for example
2[(Dimethylamino)methyl]-3,4-dihydro-7-methoxy-1(2H)-naphthaleneone or its salts e.g. its 1:1 hydrochloride.

The amount of active compound required for therapeutic effect will vary not only with the particular compound and the route of administration but also with the particular phosphodiesterase inhibitor used and its amount, i.e. with the degree of potentiation that occurs. The amount of active compound, will, however, be below that required to produce a given therapeutic effect in the absence of the potentiator and thus also below the level which would produce a significant vasodilatory effect.

In general a suitable dose of active compound in the absence of a potentiator lies in a range of from 0.01 to 200 µg per kilogram bodyweight of the recipient. In the present invention where a phosphodiesterase inhibitor is used a suitable dose of active compound will in general be less than, or about, half of the dose in the absence of potentiator e.g. in a range of from 0.002 to 100 µg per kilogram body weight.

The invention also provides a method of preparing a combination according to the invention which comprises admixing an active compound and a phosphodiesterase inhibitor.

In general the active compound and phosphodiesterase inhibitor are administered in a weight ratio of 1 part of active compound to from 1 to 200 parts of phosphodiesterase inhibitor.

While it is possible for an active compound and a phosphodiesterase inhibitor to be administered as raw chemicals, it is preferable to present them as one or more pharmaceutical formulations.

A unit dose of a formulation may contain from 0.1 mg to 20 mg e.g. from 0.2 to 16 mg of the active compound, and from 100 to 400 mg, e.g. from 250 to 350 mg, of the phosphodiesterase inhibitor.

Where the phosphodiesterase inhibitor is incorporated in a formulation of the present invention the formulation, both for veterinary and for human medical use, comprises an active compound and a phosphodiesterase inhibitor, together with one or more acceptable carriers therefor and, optionally, other therapeutic ingredient(s). When the active compound and phosphodiesterase inhibitor are to be administered separately, the prostacyclin or dihydroprostacyclin (or salt) formulation to be used comprises the active compound together with one or more acceptable carriers therefor and optionally other therapeutic ingredient(s); the phosphodiesterase inhibitor formulation may comprise a formulation in which such a compound is normally presented. The carrier must be "acceptable" in the sense of being compatible with the other ingredients of the formulation and not deleterious to the recipient.

The formulations include those suitable for oral, rectal, vaginal or parenteral (including subcutaneous, intramuscular or intravenous injection or infusion) or intrapulmonary administration, although the most suitable route in a given case will depend upon the active compound.

The formulations may conveniently be presented in unit dosage form and may be prepared by methods known in the art of pharmacy. All such methods include the step of bringing into association the active compound and the phosphodiesterase inhibitor with the carrier, which constitutes one or more accessory ingredients. In general the formulations are prepared by uniformly and intimately bringing into association, e.g. by admixing, the active compound and phosphodiesterase inhibitor with a liquid carrier or a finely divided solid carrier or both, and then, if necessary, shaping the formulation into the desired presentation.

Formulations according to the invention suitable for oral administration may be presented as discrete units such as a capsule, cachet, lozenge or tablet each containing a predetermined amount of the active compound and phosphodiesterase inhibitor as a powder or granules; or as a solution or a suspension in an aqueous or non-aqueous liquid; or as an oil-in-water emulsion or a water-in-oil liquid emulsion.

A formulation according to the invention for parenteral administration may be presented in an ampoule for receiving a defined quantity of liquid for making a solution for infusion. An example of such a parenteral formulation is a freeze dried residue of a solution of the active compound, the phosphodiesterase inhibitor and a glycine buffer of pH 10.5.

A tablet may be made by compression or moulding, optionally with one or more accessory ingredients. Compressed tablets may be prepared by compressing in a suitable machine the active compound and phosphodiesterase inhibitor in a free-flowing form, such as a powder or granules, optionally mixed with a binder, lubricant, pharmaceutically inert diluent, surface active or dispersing agent. Moulded tablets may be made by moulding in a suitable machine a mixture of the powdered active compound and a phosphodiesterase inhibitor, together with a suitable carrier moistened with a pharmaceutically inert liquid diluent.

Formulations for rectal administration may be presented as a suppository with a conventional carrier, such as cocoa butter.

Formulations suitable for vaginal administration may be presented as a pessary, cream, paste or spray formulation containing, in addition to the active compound and phosphodiesterase inhibitor, such carriers as are known in the art to be appropriate.

Formulations suitable for parenteral administration conveniently comprise a sterile aqueous preparation of the active compound and phosphodiesterase inhibitor which is preferably isotonic with the blood of the recipient.

As the active compound can be absorbed through the skin into the blood of the recipient, it may be administered topically in a topical formulation. The phosphodiesterase inhibitor may be administered by another route, unless, of course, it can be absorbed through the skin into the blood when it can be administered topically. For the treatment of wounds in or close to the skin topical administration of the formulation, with or without phosphodiesterase inhibitor, is particularly appropriate.

It should be understood that, in addition to the aforementioned ingredients, the formulations of the invention may include one or more additional ingredients, such as diluent, buffer, lubricant, or preservative (including an anti-oxidant).

According to the present invention there are further provided:

(a) A method of preventing or minimising platelet aggregation in blood, a blood product or a blood substitute which comprises contacting the blood, blood product or blood substitute with
 (a) prostacyclin, dihydroprostacyclin or a pharmaceutically acceptable salt of either of these, and with
 (b) a phosphodiesterase inhibitor.

(b) A method according to method (a) for, for example, treatment or prophylaxis of thrombosis which comprises simultaneously or sequentially administering to a mammal, including man, or to mammalian, including human, tissue
 (a) prostacyclin, dihydroprostacyclin, or a pharmaceutically acceptable salt of either of these, in an amount insufficient to produce vasodilation, and
 (b) a phosphodiesterase inhibitor.

(c) A method for use in connection with method (a) or (b) which comprises simultaneously or sequentially administering into extra-corporeal flow of blood, blood product or blood substitute
 (a) prostacyclin, dihydroprostacyclin, or a pharmaceutically acceptable salt of either of these and
 (b) a phosphodiesterase inhibitor.

(d) A method according to method (a) or (c) in which the blood, blood product or blood substitute containing the prostacyclin, dihydroprostacyclin or a salt of one of them, together with the phosphodiesterase inhibitor is treated by a cell separation process to recover at least some of cells in the blood, blood product or blood substitute.

(e) A method for prophylaxis and/or treatment of a gastric lesion in a mammal, including man, comprising the simultaneous or sequential administration of an active compound in an amount insufficient to cause vasodilation, and a phosphodiesterase inhibitor; and (f) A method for treatment of wounds in a mammal, including man, comprising the simultaneous or sequential administration of an active compound in an amount insufficient to cause vasodilation, and a phosphodiesterase inhibitor.

The following Examples illustrate the invention.

EXAMPLE 1

Thrombi were induced in the carotid artery of rabbits by the method described by R. G. Herrman and W. B. Halefield, Effects of antithrombotic drugs in in vivo experimental thrombosis in S. Sherry and A. Scriabine (eds), Platelets and Thrombosis, University Park Press, London, 1974.

After thrombus formation either an active compound, phosphodiesterase inhibitor alone or a combination of an active compound and phosphodiesterase inhibitor were infused intravenously (i.v.) for a period of time (30 minutes in the case of administration of a single compound or 30 minutes from the start of the infusion of the active compound if a combination was used), the carotid artery was cut and opened and the size of the thrombus scored on an arbitary scale (+ to +++). The absence of a thrombus was scored as −. In the case where a combination of active compound and phosphodiesterase inhibitor was used the i.v. infusion of the phosphodiesterase inhibitor was started 5 minutes before the infusion of the active compound. The active compound was infused at a sub-threshold concentration (i.e. at a concentration insufficient, when used alone, to show anti-aggregatory effects).

The results obtained are shown in Table 1. The blood pressure of the animals was monitored throughout the experiments. No effect on blood pressure was observed.

EXAMPLE 2

Rabbits were anaesthetized with pentobartitone (30 mg kg$^{-1}$ i.v.) and heparin (2500 IU kg$^{-1}$ i.v.) was injected immediately prior to exteriorization of blood. Arterial blood from a carotid artery of the rabbits was withdrawn continuously at 3 ml min$^{-1}$ by a roller pump and used to superfuse collagen strips excised from the Achilles tendon of another rabbit.

The tendons were suspended freely from auxotonic transducers (see Paton W. D. M. J. Physiol., 1957, 137, 35P), the outputs of which depended on the weight of the tendon and were displayed on a multi-channel pen recorder. Platelets, and possibly other cells, stuck during the superfusion of the tendon, strips, thereby increasing their weights. Changes in weight due to platelet aggregation and/or adhesion were recorded as deflections of the pens, previously calibrated in milligrams. After superfusing the tendons, the blood was returned intravenously to the rabbit by gravity.

TABLE 1

| Active Compound and Concentration | Phosphodiesterase Inhibitors and Concentration | Thrombus size | Artery |
|---|---|---|---|
| Prostacyclin at 50ng/min/kg | None | +++ | L.C. |
|  | 3-Isobutyl-1-methyl xanthine at 10 µg/min/kg | + | R.C. |
| Prostacyclin at 25ng/min/kg | None | ++ | L.C. |
|  | 3-Isobutyl-1-methyl xanthine at 50 µg/min/kg | — | R.C. |
| Prostacyclin at 25ng/min/kg | None | +++ | L.C. |
|  | Theophylline at 125 µg/min/kg | — | R.C. |
| Prostacyclin at 10ng/min/kg | None | +* | R.C. |
|  | Theophylline at 125 µg/min/kg | — | L.D. |
| Prostacyclin at 25ng/min/kg | None | ++ | L.C. |
|  | Theophylline at 125 µg/min/kg | + | R.C. |
| Prostacyclin at 10ng/min/kg | None | ++ | L.C. |
|  | Theophylline at 200 µg/min/kg | + | R.C. |
| None | None | +++ | L.C. |
| Prostacyclin at 10ng/min/kg | Theophylline at 200 µg/min/kg | + | R.C. |
| None | None | +++ | R.C. |
|  | Theophylline at 200 µg/min/kg | +++ | L.C. |
| Dihydroprostacyclin at 50ng/min/kg | None | +++ |  |
| Dihydroprostacyclin at 100ng/min/kg | None | +(2 experiments) |  |
| Dihydroprostacyclin at 250ng/min/kg | None | — |  |
| Dihydroprostacyclin at 50ng/min/kg | None | ++ | L.C. |
|  | Theophylline at 200 µg/min/kg | ++ | R.C. |
| Dihydroprostacyclin at 50ng/min/kg | None | +++ | L.C. |
|  | Theophylline at 200 µg/min/kg | + | R.C. |
| Dihydroprostacylcin at 50ng/min/kg | None | +++ | L.C. |
|  | Theophylline at 200 µg/min/kg | — | R.C. |

*1 hour 15 minutes elapsed before infusion of active compound started.

When the blood superfusion over the tendon was started and tendon strips accumulated cell aggregates and increased in weight over a period of from 35 to 40 minutes. Thereafter there was no further increase in weight; the average increase in weight was 193±15 mg; n=19 (n is the number of experiments).

In the following experiments, the superfused tendon strips were allowed, as above, to reach a stable increase in weight due to cell deposition. Any subsequent loss of weight then indicated disaggregation of cells. Prostacyclin sodium salt, [See Johnson, R. A., Lincoln, F. H., Thompson, J. L., Nidy, E. G., Mizsak, S. A., Axen, U. J. Am. Chem. Soc., 1977, 99, 4182], was dissolved in Tris buffer (50 mM pH 7.4) and infused (0.1-1 ng ml$^{-1}$ of blood for 3 minutes) into the blood bathing the tendons. This induced disaggregation of cells which was dose-dependent and reversible; 0.1 ng ml$^{-1}$ of prostacyclin in the arterial blood induced 26±3 mg (n=10) disaggregation in arterial blood, and 1 ng ml$^{-1}$ induced 86±6 mg (n=6) disaggregation.

Dipyridamole was infused into the blood superfusing the tendons and also induced a dose-dependent and reversible disaggregation.

Dipyridamole and prostacyclin were infused together into the blood superfusing the tendons and produced a clear synergism of their individual disaggregating effects.

The concentrations of prostacyclin sodium and of dipyridamole used in the comparison are shown in Table 2, along with the disaggregations obtained, expressed as a percentage of the maximum disaggregation that could theoretically be obtained (i.e. the difference in weight between the tendon with maximum aggregation and the initial weight of the tendon).

EXAMPLE 3

A freeze-dried formulation was prepared by dissolving dihydroprostacyclin sodium salt (1 mg) and dipyridamole (300 mg) in solution in Water for Injections (European Pharmacopoeia) which contained a glycine buffer of glycine (0.025 M) and sodium chloride (0.025 M). The solution obtained was adjusted to pH 10.5 with sodium hydroxide, which formed part of the buffer, and then freeze-dried.

Just before use the freeze-dried material is reconstituted in Water for Injections and then administered by infusion or perhaps by injection.

EXAMPLE 4

This was carried out as Example 3 except that the 1 mg of dihydroprostacyclin sodium was replaced by 8 mg of the dihydroprostacyclin sodium.

TABLE 2

| Prostacyclin sodium infusion, concentration ng ml$^{-1}$ of blood | Prosphodiesterase Inhibitor and concentration | % Disaggregation of platelet aggregate in arterial blood ± s.e.m. | No. of expts. No. of expts. |
|---|---|---|---|
| None | Dipyridamole 1 µg ml$^{-1}$ single dose | 10 ± 1 | 14 |
| 0.05 | None | 2 | 8 |
|  | Dipyridamole 1 µg ml$^{-1}$ single dose | 28 ± 2 | 6 |
| 0.1 | None | 15 ± 1 | 10 |
|  | Dipyridamole 1 µg ml$^{-1}$ single dose | 38 ± 5 | 6 |
| 0.5 | None | 22 ± 2 | 10 |
|  | Dipyridamole 1 µg ml$^{-1}$ single dose | 45 ± 3 | 6 |

EXAMPLES 5 AND 6

These were carried out as Examples 3 and 4 respectively, except that the dihydroprostacyclin sodium was replaced by an equal weight of prostacyclin sodium.

What we claim is:

1. A method for prophylaxis and/or treatment of a gastric lesion in a mammal, which comprises simultaneously or sequentially internally administering 1 part by weight of (a) a compound selected from the group consisting of prostacyclin, dihydroprostacyclin, and their pharmaceutically acceptable salts, in an amount insufficient to cause vasodilation, and 1 to 200 parts by weight of (b) a phosphodiesterase inhibitor selected from the group consisting of theophylline, 3-isobutyl-1-methyl xanthine, dipyridamole, a pharmaceutically acceptable salt of theophylline, a pharmaceutically acceptable salt of dipyridamole, and a pharmaceutically acceptable salt of 3-isobutyl-1-methyl xanthine.

2. A method for the treatment of a gastric lesion in a mammal which comprises the internal administration of an effective gastric lesion treatment amount of 1 part by weight of sodium prostacyclin and 1 to 200 parts by weight of a phosphodiesterase inhibitor selected from the group consisting of theophylline, 3-isobutyl-1-methyl xanthine, dipyridamole, a pharmaceutically acceptable salt of theophylline, a pharmaceutically acceptable salt of dipyridamole, and a pharmaceutically acceptable salt of 3-isobutyl-1-methyl xanthine.

3. The method of claim 1 in which the inhibitor is theophylline or a pharmaceutically acceptable salt thereof.

4. The method of claim 2 in which the inhibitor is 3-isobutyl-1-methyl xanthine or a pharmaceutically acceptable salt thereof.

* * * * *